United States Patent
Mora et al.

(10) Patent No.: US 6,512,093 B1
(45) Date of Patent: Jan. 28, 2003

(54) METHOD OF PREPARING LIPOPROTEINS FROM FATTY ACIDS PRESENT IN OLIVE OIL

(75) Inventors: Valtiero Mora, Brescia (IT); Palmiro Comini, Castiglione Delle Stiviere (IT); Gianbattista Rastrelli, Manerba Del Garda (IT)

(73) Assignees: Keminova Italiana s.r.l., Botticino Sera (BS) (IT); Maycos Italiana s.a.s., Castiglione Delle Stiviere (MN) (IT)

( * ) Notice: Subject to any disclaimer, the term of this patent is extended or adjusted under 35 U.S.C. 154(b) by 0 days.

(21) Appl. No.: 09/555,867
(22) PCT Filed: Dec. 7, 1998
(86) PCT No.: PCT/IT98/00351
  § 371 (c)(1),
  (2), (4) Date: Jun. 7, 2000
(87) PCT Pub. No.: WO99/29814
  PCT Pub. Date: Jun. 17, 1999

(30) Foreign Application Priority Data

Dec. 10, 1997 (IT) .................... RM97A0765

(51) Int. Cl.⁷ ............................... C07K 1/107
(52) U.S. Cl. ............ 530/345; 530/333; 530/359; 530/370; 514/2
(58) Field of Search ................ 530/333, 345, 530/359, 370; 514/2

(56) References Cited

U.S. PATENT DOCUMENTS 5,916,577 A * 6/1999 Golz .................... 424/401
5,945,299 A * 8/1999 von Kries ............. 435/68.1
6,004,771 A * 12/1999 Thornton ................. 435/29

FOREIGN PATENT DOCUMENTS

| GB | 385 957 A | 4/1931 |
| GB | 462 977 | 3/1937 |
| GB | 792 576 A | 2/1958 |
| WO | 94 27561 A | 8/1994 |

OTHER PUBLICATIONS

Sacchi (Magn. Reson. Chem 35, S133–S145, 1997).*

* cited by examiner

Primary Examiner—Christopher S. F. Low
Assistant Examiner—David Lukton
(74) Attorney, Agent, or Firm—DeLio & Peterson, LLC

(57) ABSTRACT

A method of preparing lipoproteins, lipoaminoacids, lipid esters, and glucolipids from olive oil or one or more of its constituting fatty acids which are condensed with vegetal protein hydrolyzates or aminoacids or esterificated with alcohols or sugars, said fatty acids being chlorinated fatty acids of the olive oil.

4 Claims, No Drawings

METHOD OF PREPARING LIPOPROTEINS FROM FATTY ACIDS PRESENT IN OLIVE OIL

FIELD OF THE INVENTION

The present invention relates to a method of preparing a set of substances having new characteristics for use especially in the production of a very large range of products such as cosmetics, drugs, foods (emulsions, creams, milks, ointments, shampoos, cleansing means for face/body, bath foams, etc.) industrial products (detergents for washing-machines, dishwashing machines, all-purpose cleansing agents), and chemical-pharmaceutical products (solvents, dispersing agents, emulsifiers for aerosol, inhalations, environment deodorizers).

These preparations can be used under absolute safety conditions regarding both toxicological-allergic and environment-friendly aspects since their constituents are already present in nature.

SUMMARY OF THE INVENTION

The products prepared by the method according to the invention can be considered to belong to four main groups, namely lipoproteins, lipoaminoacids, lipid esters, and glucolipids.

The preparation of such groups starts from chlorides of fatty acids, particularly the individual fatty acids forming the olive oil or a mixture of such fatty acids.

Among the fatty acids of the olive oil used individually or in combination in the method according to the invention oleic acid, palmitic acid, myristic acid, and stearic acid have the greatest importance. Such acids are condensed with vegetal protein hydrolysates to provide lipoproteins, with aminoacids to provide lipoaminoacids, with alcohols to provide lipid esters, and with sugars to provide glucolipids.

BEST MODE OF CARRYING OUT THE INVENTION

Some examples of the method according to the invention will be described herebelow.

In a preferred embodiment of the method of preparing a lipoprotein of fully vegetal nature with a large range of applications, as explained thereafter, the following steps are carried out by using a hydrolyzed vegetal protein, namely wheat gluten which is enzymatically hydrolyzed, in the condensation of the fatty acids of olive oil:

An enzymatic hydrolyzate solution of wheat gluten (60–80% by weight referred to the finished product) is fed into a mixer of stainless steel and brought to a temperature between 45° C. and 70° C.; the following substances in the indicated proportions are added under stirring:

| L.ascorbic acid | 0.1–0.4% |
| glycerol | 4–11% | and 2–4% potassium hydrate or sodium hydrate water solution having a concentration between 20 and 35% until a pH between 7.5 and 9.5 is reached while keeping the temperature at the initial value.

More particularly a substance with optimum characteristics is obtained by carrying out the following Example.

An amount of gluten hydrolisate equal to 70% by weight of the finished product is fed into a mixer of stainless steel and heated at 55° C. under stirring. When such temperature is reached, 0.3% L. ascorbic acid, 0.3% sodium EDTA, 10% glycerol, and 30% potassium hydrate (KOH) water solution are added until pH 8.5 is reached.

After about 15 minutes the reaction is started by adding 6% by weight of chlorinated fatty acids of olive oil still under stirring at constant temperature and the above pH 8.5 which is kept by a continuous, very gradual addition of 8% potassium hydrate solution (30% water solution) . The reaction is continued under stirring at constant temperature for about 2 hours followed by a slow cooling. Finally, pH is adjusted to 7 by adding a total amount of 1% phosphoric acid and citric acid in a ratio of 1:1.

In order to obtain a lipoaminoacid to be used according to the applications of the present invention, the following method has been carried out by using a derivative of glutamic acid as aminoacid, namely sodium glutamate, and employing the following substances in the indicated weight proportion ranges: An amount of 30–42% distilled water, 10–17% sodium glutamate, 0.1–0.5% sodium EDTA, 8–11% 95°-ethyl alcohol are mixed in a reactor of stainless steel. Under stirring the mixture is brought to a temperature between 45° C. and 75° C. by adding very gradually an amount of 12–20% of a 30% potassium hydrate water solution and 16–25% chlorinated fatty acids of olive oil taking care of keeping pH between 8 and 12 and the temperature at the initial value. The reaction is continued for 2 to 5 hours followed by a cooling of the whole mixture and citric acid is added to adjust pH to 7–8. Finally, ethyl alcohol is distilled and the balance to 100 is formed by adding distilled water.

Therefore, a lipoaminoacid having essentially the same characteristics as the lipoprotein both as far as its essential features and applications is concerned but capable of producing a persistent, creamy, more abundant foam has been prepared by the above-mentioned method.

A lipoaminoacid having the desired characteristics to an optimum extent has been prepared by reacting the above-mentioned substances as indicated above in the amounts of the following Example:

Example of Lipoaminoacid:

In a reactor of stainless steel the following substances are mixed:

| Distilled water | 36, 7% |
| Sodium glutamate | 14% |
| Sodium EDTA | 0.3% |
| 95°-Ethyl alcohol | 10% |

The mixture contained in the reactor is brought to 65° C. under stirring and:

| 30% KOH water solution | 17% |
| Chlorinated fatty acids of olive oil | 21% | are gradually added still under stirring and keeping pH to 9.5.

The reaction is continued for 3 hours and after cooling citric acid is added until pH 7.5 is reached. Finally, ethyl alcohol is distilled and the balance to 100 of the final product is formed by adding distilled water.

In order to obtain a lipid ester to be used according to the applications of the invention, the following method has been carried out by using a fatty alcohol, namely oleic alcohol, and employing the following substances in the indicated weight proportion ranges: Oleic alcohol is fed into a reactor of stainless steel provided with stirrer and distiller and, after having brought the temperature to 60–96° C., chlorinated oleic acid is added, the ratio between oleic alcohol and oleic acid being 1:0.8–1:1.5. HCl fumes developed during the reaction are then recovered by feeding them to a separated alkali solution.

It should be noted that the addition of chlorinated oleic acid must be gradual and very slow so as to be concluded in a period of 2–5 hours. The reaction is continued for 3–5 hours by keeping the initial temperature constant. The distillation of the hydrochloric acid should be complete. A washing is carried out in the end by mixing with distilled water in a proportion of about 20% of the total mass that is eventually discharged from the bottom of the reactor.

A lipid ester having essentially the desired characteristics was prepared by the above-mentioned method.

A lipid ester essentially having the desired characteristics was prepared by reacting the above-mentioned substances according to the described method in the amounts listed in the following Example:

Example of Lipid Ester:

Under the above-mentioned conditions oleic alcohol adjusted to 90° and chlorinated oleic alcohol in the ratio of 1:1.1 are fed by adding the latter very slowly during 4 hours into a reactor of stainless steel provided with stirrer and distillator. The mixture is reacted for a further 4 hours still at temperature of 90° C. under distillation of the hydrochloric acid by conveying the HCl fumes to an alkali solution. The washing with 20% distilled water is carried out at the end of the distillation, as indicated above.

By the Example described above a light, clear, colourless, stable to the oxidation, non-fatty oil is obtained so that quite soft, delicate cosmetics and dermatologic products, oils, emulsions, lipogels etc. provided with excellent feel, softness and dermic compatibility can be prepared.

In the following method the chlorides of the olive oil acids are condensed with sugars derived, for example, from enzymatic hydrolysis of starch, barley, wheat and the like.

In order to prepare a glucolipid to be used according to the applications of the present invention, the following method has been carried out by using tetraose malt as sugar and employing the following substances in the indicated weight-proportion ranges: An amount of 38–45% distilled water and 18–36% tetraose malt produced by enzymatic hydrolysis of a starch are fed into a reactor of stainless steel; an amount of 9–18% 95°-ethyl alcohol referred to the finished product is added under stirring and the whole : mixture is brought to a temperature between 45 and 75° C. by adding 0.1–0.5% sodium EDTA and then very gradually 7–15% chlorinated oleic acid and 3–7% of a 30%-solution of sodium hydrate taking care of keeping pH between 7 and 9.

The reaction is continued for 2–5 hours still under stirring at the initial temperature. Final pH is adjusted between 6 and 8 and alcohol is distilled forming the balance to 100 by adding distilled water. A glucolipid having the desired characteristics to an optimum extent has been prepared by reacting the above-mentioned substances as indicated above in the amounts of the following Example:

Example of glucolipid:

In a reactor of stainless steel the following substances are mixed:

| | |
|---|---|
| Distilled water | 46% |
| Tetraose malt | 24% |
| 95°-Ethyl alcohol | 15% |
| Sodium EDTA | 0.3% |

Still under stirring and bringing the content of the reactor to a temperature of 65° C. an amount of 10% chlorinated oleic acid and 4.5% of a 30% NaOH water solution are gradually added keeping pH to 8.5.

The reaction is continued for 3 hours and thirty minutes and citric acid is added under constant temperature until pH 7.5 is reached. Finally, ethyl alcohol is distilled and the balance to 100 of the final product is formed by adding distilled water.

INDUSTRIAL APPLICABILITY

The finished product showed eudermic properties perfectly tolerated also by the most delicate skins and the mucosa. Furthermore it has hydrating, emollient, protective properties and, as far as its inherent cleansing activity is concerned, it is also suitable for the preparation of cleansing creams and milks, shampoos, bath foams, personal cleanliness products and, more particularly, paedocosmetics.

What is claimed is:

1. A method of preparing a mixture of lipoproteins comprising the steps of:
   (a) reacting a first mixture of chlorinated fatty acids of olive oil with a second mixture comprising a vegetal protein hydrolyzate for a time and under conditions effective to form a mixture of lipoproteins,
      wherein said mixture of chlorinated fatty acids is obtained by chlorinating a mixture of all fatty acids present in olive oil; and
   (b) isolating the mixture of lipoproteins of step (a).

2. The method according to claim 1 for preparing a mixture of lipoproteins comprising the steps of:
   (a) introducing an enzymatic hydrolyzate solution of a vegetable protein into a mixer;
   (b) setting the temperature of the enzymatic hydrolyzate solution to 45° C.–75° C.;
   (c) adding L-ascorbic acid and glycerol to a final concentration of about 0.1–0.4% and 4–11%, respectively;
   (d) adjusting the pH of the resulting solution from steps (a), (b) and (c) to 7.5–9.5 by adding an aqueous solution of 20–35% KOH or NaOH to the solution while maintaining the temperature within the range of 45–70° C.;
   (e) adding the chlorinated fatty acids of olive oil to the solution of step (d);
   (f) reacting the chlorinated fatty acids of olive oil and hydrolyzed vegetable protein for a time and under conditions to form a mixture of lipoprotein reaction products; and
   (g) isolating the resulting lipoprotein reaction product mixture.

3. A method for preparing a mixture of lipoproteins comprising the steps of:
   (a) obtaining a hydrolyzate solution by enzymatic hydrolysis of gluten;
   (b) setting the gluten hydrolyzate to a temperature of about 55° C. with stirring;
   (c) adding L-ascorbic acid and glycerol in an amount to a final concentration of about 0.30% and 10%, respectively, and further adding sodium ethylene diamine tetraacetic acid in an amount of about 0.3%;

(d) adding a solution of 30% KOH in water solution until a pH of 8.5 is reached;

(e) stirring the resulting mixture for 15 minutes and then adding chlorinated fatty acids of olive oil under stirring in an amount in a final concentration of about 6% by weight and keeping the temperature and pH constant by further adding continuously and gradually a 30% KOH water solution in an amount of about 8% of the reaction mixture;

(f) continuing the reaction under stirring at a constant temperature for about 2 hours followed by slow cooling;

(g) adjusting the pH of the mixture to about 7 by adding phosphoric acid and citric acid in a ratio of 1:1; and (h) isolating the mixture of lipoproteins from the reaction product mixture.

4. The method according to claim 3 wherein the weight ratio of protein to fatty acyl group in the lipoprotein is 70:30.

* * * * *